United States Patent
Ohue et al.

(10) Patent No.: US 8,435,188 B2
(45) Date of Patent: May 7, 2013

(54) EYE OPENING DETECTION SYSTEM AND METHOD OF DETECTING EYE OPENING

(75) Inventors: Kenichi Ohue, Toyota (JP); Yuji Ninagawa, Nishikamo-gun (JP); Kentaro Takahashi, Toyota (JP); Shin-ichi Kojima, Nisshin (JP); Jun Adachi, Okazaki (JP); Tomoharu Suzuki, Anjo (JP)

(73) Assignees: Toyota Jidosha Kabushiki Kaisha, Toyota-shi (JP); Aisin Seiki Kabushiki Kaisha, Kariya-shi (JP)

( * ) Notice: Subject to any disclaimer, the term of this patent is extended or adjusted under 35 U.S.C. 154(b) by 636 days.

(21) Appl. No.: 12/443,775

(22) PCT Filed: Nov. 6, 2007

(86) PCT No.: PCT/IB2007/003369
§ 371 (c)(1),
(2), (4) Date: Mar. 31, 2009

(87) PCT Pub. No.: WO2008/056229
PCT Pub. Date: May 15, 2008

(65) Prior Publication Data
US 2010/0094176 A1    Apr. 15, 2010

(30) Foreign Application Priority Data
Nov. 6, 2006  (JP) .................................. 2006-300951

(51) Int. Cl.
*A61B 5/00*   (2006.01)
(52) U.S. Cl.
USPC .............. 600/558; 600/595; 348/78; 382/117

(58) Field of Classification Search .................. 382/107, 382/103, 104, 117, 118; 600/595, 558; 348/78
See application file for complete search history.

(56) References Cited

U.S. PATENT DOCUMENTS

| | | | |
|---|---|---|---|
| 6,393,136 B1 * | 5/2002 | Amir et al. ..................... 382/103 |
| 2001/0036298 A1 * | 11/2001 | Yamada et al. ................ 382/118 |
| 2005/0073136 A1 | 4/2005 | Larsson et al. |
| 2006/0203088 A1 | 9/2006 | Hammoud et al. |
| 2006/0204041 A1 * | 9/2006 | Hammoud et al. ............ 382/107 |
| 2006/0204042 A1 | 9/2006 | Hammoud et al. |

FOREIGN PATENT DOCUMENTS

| | | |
|---|---|---|
| EP | 1 700 567 | 9/2006 |
| EP | 1 701 288 | 9/2006 |
| EP | 1 701 289 | 9/2006 |
| JP | 6 319701 | 11/1994 |
| JP | 2000 102510 | 4/2000 |
| JP | 2005 251224 | 9/2005 |
| JP | 2005 296349 | 10/2005 |

(Continued)

*Primary Examiner* — Max Hindenburg
(74) *Attorney, Agent, or Firm* — Oblon, Spivak, McClelland, Maier & Neustadt, L.L.P.

(57) ABSTRACT

An eye opening detection system that includes an imaging mechanism that captures an image of the face of a detected subject, an edge extraction mechanism that extracts the edge of the image captured, and an upper and lower eyelid detection mechanism that detects the upper and lower eyelids of the detected subject according to the edge extracted, and that detects the eye opening of the detected subject with reference to a detected distance between the upper and lower eyelids. The upper and lower eyelid detection detects the upper eyelid and detects the lower eyelid with reference to the upper eyelid detected.

15 Claims, 2 Drawing Sheets

FOREIGN PATENT DOCUMENTS

| | | |
|---|---|---|
| JP | 2006 120006 | 5/2006 |
| JP | 2006 163900 | 6/2006 |
| JP | 2006 178676 | 7/2006 |
| JP | 2006 251926 | 9/2006 |
| JP | 2006 268189 | 10/2006 |
| JP | 2006 277192 | 10/2006 |
| JP | 2006 285715 | 10/2006 |
| JP | 2006277192 A * | 10/2006 |

* cited by examiner

EYE OPENING DETECTION SYSTEM AND METHOD OF DETECTING EYE OPENING

BACKGROUND OF THE INVENTION

1. Field of the Invention

The present invention relates to an eye opening detection system for detecting eye openings of a detected subject and a method thereof.

2. Description of the Related Art

The eye opening detection system described in Japanese Patent No. 3383594 uses a technique for detecting the upper edge of a lower eyelid and then detecting the lower edge of the upper eyelid of a subject. The system described in Japanese Patent No. 3383594 scans pixels on a measuring line from the range where a threshold value for the detection of an iris edge point is acquired to the lower direction at first and detects the upper edge of the lower eyelid as a pixel position that density exceeds the threshold value for the detection of the iris edge point. Also, the system scans pixels on a measuring line from an upper edge of a pupil to the upper side thereof and detects the lower edge of the upper eyelid as a pixel position that density exceeds the threshold value for the detection of the iris edge point. Here, the threshold value for the detection of the iris edge point is set based on the maximum value of the density detected by the scanning from the lower edge of the pupil to the lower direction.

Although it is necessary to detect the upper and the lower eyelids for the detection of the eye opening of a detected subject, the lower eyelid has fewer characteristics in shape than the upper eyelid, and therefore, it is more difficult to detect the lower eyelid. The invention described in Japanese Patent No. 3383594 detects the lower eyelid first and then detects the upper eyelid, and consequently it may lead to a false detection of the lower eyelid and deterioration in a detection accuracy of the eye opening.

SUMMARY OF THE INVENTION

The present invention provides an eye opening detection system and a method thereof that appropriately prevents the false detection of the lower eyelid and accurately detects the eye opening.

A first aspect of the present invention is directed to an eye opening detection system that includes an imaging means for capturing an image of the face of a detected subject; an edge extraction means for extracting the edge of the image captured; and upper and lower eyelid detection means for detecting the upper and lower eyelids of the detected subject according to the edge extracted, and that detects the eye opening of the detected subject with reference to a distance between the upper eyelid and the lower eyelid detected, in which the upper and lower eyelid detection means detects the upper eyelid and then detects the lower eyelid with reference to the upper eyelid detected.

According to the first aspect, the present invention focuses on the fact that the better detection rate can be obtained at the detection of the upper eyelid having an arc shape during opening of the eye than the lower eyelid having a linear shape in both opening and closing of the eye. Therefore, the present invention appropriately prevents the false detection of the lower eyelid and accurately detects the eye opening by detecting the lower eyelid with reference to the upper eyelid that has been detected.

The imaging means may be disposed in a position lower than the eyes of the detected subject in the vertical direction. With the above construction, when the imaging means captures the image of the detected subject from below, the upper eyelid can be detected more clearly than the lower eyelid. Therefore, the detection accuracy of the upper eyelid can be improved. The detection accuracy of the lower eyelid can also be improved with reference to the upper eyelid that has been accurately detected.

The detected subject may be an operator of a vehicle, and the imaging means may be disposed in a position lower than a headrest disposed on an operator's seat in a vertical direction. With the above construction, the imaging means can appropriately capture the image of the operator of the vehicle from below.

A lighting means illuminating the face of the detected subject may be further provided, and the lighting means may be disposed at a position lower than the eyes of the detected subject in a vertical direction.

With the above construction, when the lighting means illuminates the face of the detected subject from below, the shadow created by the light is cast upward, and thus the upper eyelid can be detected more clearly than the lower eyelid. Therefore, the detection accuracy of the upper eyelid can be improved. The detection accuracy of the lower eyelid can also be improved with reference to the upper eyelid that has been accurately detected.

The detected subject may be an operator of a vehicle, and the lighting means may be disposed in a position lower than a headrest disposed on an operator's seat in a vertical direction. With the above construction, the lighting means can appropriately illuminate the operator of the vehicle upward from below.

In addition to the imaging device described above serving as a first imaging means, the eye opening detection system may include an additional imaging means as second imaging means, in which the edge extraction means extracts the edge of the image acquired by at least one of the first imaging means and the second imaging means, and the upper and lower eyelid detection means detects the upper eyelid with respect to the image acquired by at least the first imaging means between the first and the second imaging means and detects the lower eyelid as well with reference to the upper eyelid detected.

The second aspect of the present invention is directed to an eye opening. detection method of detecting an eye opening of a detected subject, including the steps of acquiring an image of a face of a detected subject, extracting an edge of the image of the face acquired, detecting an upper eyelid of the detected subject according to the edge extracted, and detecting a lower eyelid of the detected subject with reference to the upper eyelid detected.

According to the second aspect, because a better detection rate can be obtained at the detection of the upper eyelid having an arc shape during opening of the eye than the lower eyelid having a linear shape in both opening and closing of the eye, the second aspect can appropriately prevent the false detection of the lower eyelid and accurately detect the eye opening by detecting the lower eyelid with reference to the upper eyelid that has been detected.

Accordingly, the present invention provides an eye opening detection system and a method thereof that appropriately prevents the false detection of the lower eyelid and accurately detects the eye opening.

BRIEF DESCRIPTION OF THE DRAWINGS

The foregoing and further features and advantages of the invention will become apparent from the following descrip

DETAILED DESCRIPTION OF THE EMBODIMENTS

An example embodiment of the present invention will be described hereinafter with reference to the drawings.

Figure 1:
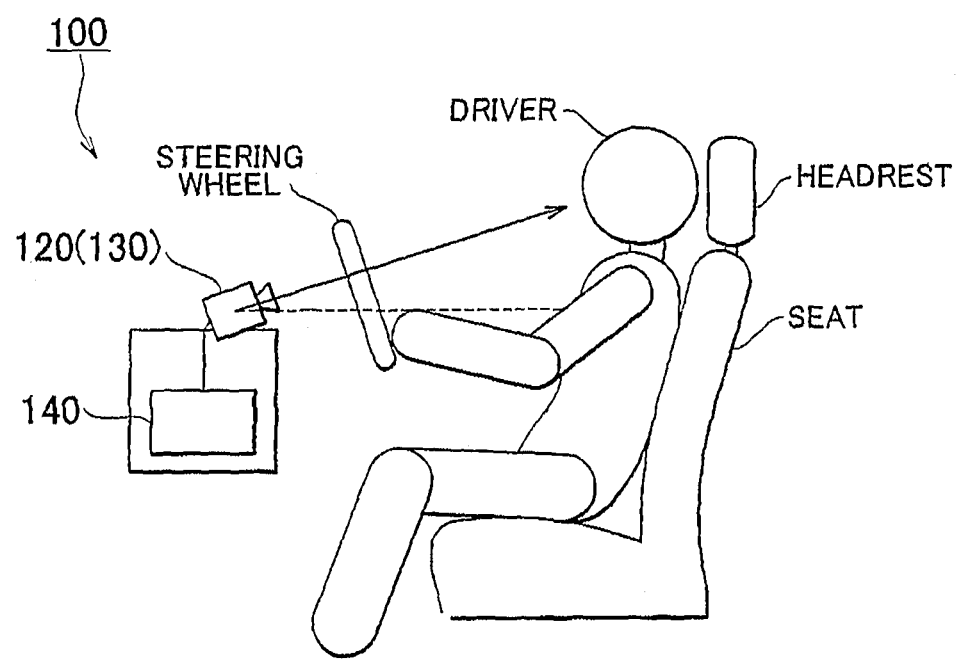
- FIG. 1 is a schematic diagram showing a principal construction of an embodiment of the eye opening detection system according to the present invention.

FIG. 1 is a schematic diagram showing a principal construction of an embodiment of the eye opening detection system according to the present invention. The eye opening detection system 100 of the present embodiment includes imaging means 120 for capturing an image of the face of the detected subject, and an image-processing device 140.

The imaging means 120 may be a camera that includes a sensor array having, for example, a charge-coupled device (CCD) or a complementary metal oxide semiconductor (CMOS) as an image pickup device. The imaging means 120 may be adapted to acquire a gray-scale image (for example, a 256-level gray-scale image). The imaging means 120 is disposed at an appropriate position in a vehicle so as to capture the front of a driver (for example, a face of the driver from the front). The imaging means 120 may be disposed at a position lower than the eyes of the driver in the vertical direction. That is, when the detected subject is a driver as the present embodiment, the imaging means 120 may be disposed at a position lower than the headrest provided on a driver's seat in the vertical direction. In addition, the optical axis of this imaging means 120 is inclined upward, and for example, the imaging means 120 may be disposed on the steering column Or in the instrument cluster so as to capture the face of the driver with an optical axis directed upward. Such a configuration can accurately detect the upper eyelid of the driver as described later. The imaging means 120 may be adapted to acquire the image of the driver's face (hereinafter referred to as "face image") in real time while the vehicle is in motion and to supply the image to the image-processing device 140 exemplarily at a rate of 30 frames per second (fps).

The imaging means 120 may have lighting means 130 for illuminating the face of the driver. The lighting means 130 may emit near-infrared light, for example. The lighting means 130 may be disposed at an appropriate position in a vehicle so as to illuminate the front of the driver (for example, the face of the driver from the front). The lighting means 130 may be disposed at a position lower than the eyes of the driver in the vertical direction, in a similar manner to the imaging means 120. That is, when the detected subject is a driver as the present embodiment, the lighting means 130 may be disposed in a position lower than the headrest disposed on a driver's seat in the vertical direction. In addition, the optical axis of the lighting means 130 is inclined upward and arranged upward to illuminate the face of the driver from below. Such a configuration can accurately recognize the upper eyelid of the driver as described later. The lighting means 130 may also be integrated with the imaging means 120 as shown in FIG. 1, and the optical axes of the imaging means 120 and the lighting means 130 may be arranged in the same direction.

The image processing device 140 is primarily built with an appropriate processor (for example, a digital signal processor (DSP)) or a microcomputer as its hardware construction, and includes a CPU for performing various image processing as described later, ROM for storing a program and data used for performing the various image processing as described later, readable/writable RAM for storing computational results and the like, a timer, a counter, an input interface, an output interface, and the like.

Figure 2:
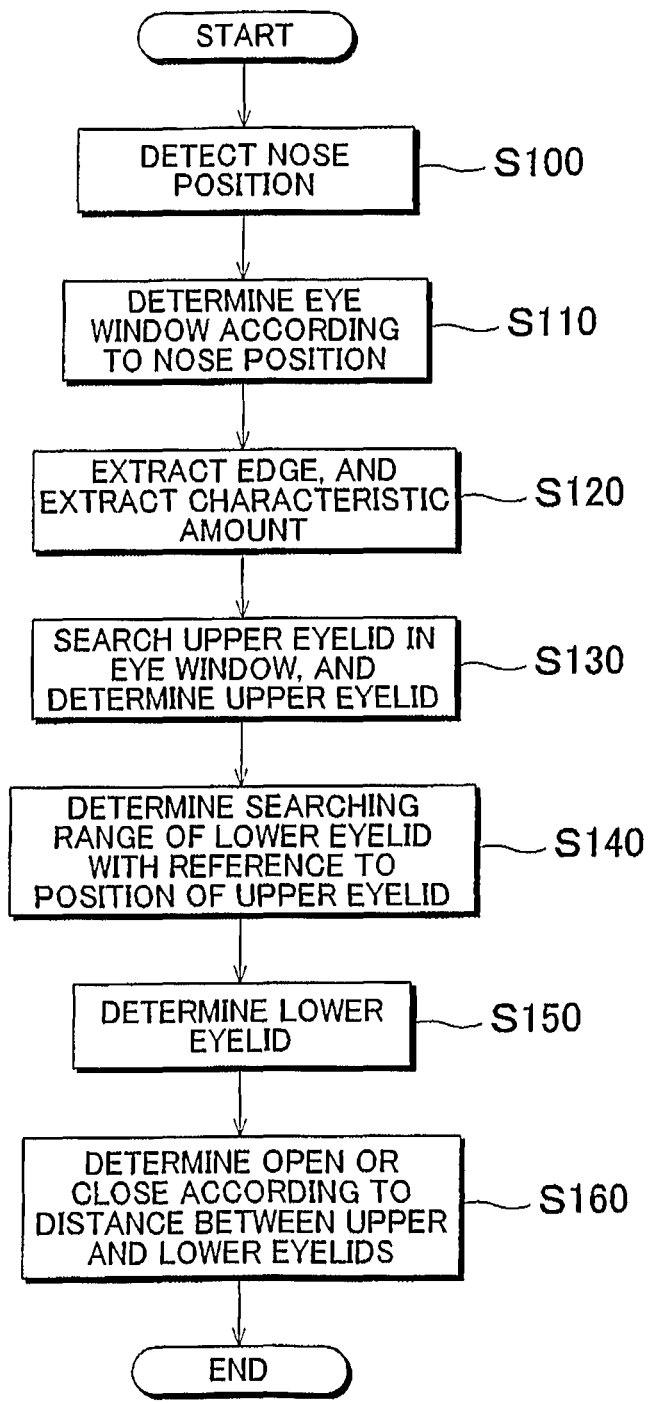
FIG. 2 is a flowchart showing principal processes performed by an image-processing device 140.

FIG. 2 is a flowchart showing principal operations performed by the image processing device 140.

In step S100, a nose position is detected in the face image. The nose position may be detected based on the position of the nostrils as the characteristic, for example. In this embodiment, because the imaging means 120 captures the face of the driver from below to acquire the face image as described above, the nostrils may be detected when the driver maintains a normal posture (unless the driver excessively bend the head down, for example).

In step S110, the position of an eye window is determined according to the detected nose position. The position of the eye window is appropriately determined according to the geometrical positional relation between the nose and the eye. For example, the eye window is defined at two positions in the upper part of the image around the nose position. Although the eye window has the size that can cover the whole area of an eye, the size of the eye window is defined with a margin in consideration of the condition that there are individual differences in the relative position between eyes and nose in a face or that the relative position between eyes and nose in a particular driver can vary depending on the change in a facing direction.

In step S120, edge extraction operation and characteristic amount extraction operation are performed for the area in the eye window. The edge extraction operation may be performed by applying Sobel's edge detection algorithms, for example. The lateral edge in the eye window is extracted by using a common 3×3 Sobel filter. Hereinafter, in all the extracted lateral edges, the lateral edge extracted due to the transition of the density from white, to black in the direction from top to bottom on a vertical line is referred to as "white-black edge", and the lateral edge extracted due to the transition of the density from black to white is referred to as "black-white edge", for convenience.

The characteristic amount extraction operation may be performed for example as described below. First, a sum of intensity (a sum of density) of the lateral edge is evaluated for each horizontal line, and the lateral edge where the sum of intensity of the lateral edge reaches a peak (or the lateral edge constituting a peak in a histogram of the lateral edge) is extracted.

In step S130, a search window is moved in the eye window, and the position of the upper eyelid is determined according to the result of the edge extraction processing and the characteristic amount extraction processing. The search window may be defined according to the pixel range that represents the upper eyelid and is derived from the experiment and the like in advance. The search window may be about 1×15 pixels (1 pixel in vertical direction and 15 pixels in horizontal direction) and appropriately defined corresponding to resolution, scaling, and the like, for example. More specifically, while the search window is moved in the eye window, the sum of the intensity of the lateral edge in the search window is calculated, and the lateral edge (white-black edge) in the search window at the position where the sum of the intensity of the lateral edge is the predetermined value or greater is recognized as an "upper eyelid candidate". In this case, if there are upper eyelid candidates adjacently lying above and below, the uppermost upper eyelid candidate is selected. Furthermore, if there is an upper eyelid candidate near the top of the eye window, such candidate will also be discarded. This is because the eye window is defined large as described above and there is a case that the lateral edge representing an eyebrow exists around the top of the window. The remaining upper eyelid candidate is then recognized as the lateral edge representing the upper eyelid.

Alternatively, the edge representing the upper eyelid may be extracted based on the characteristic in shape of the upper eyelid, which is generally in an arc shape when the eye is open. In other words, the edge continuously extending in approximately horizontal direction in an arc shape (the edge that the color thereof changes from white to black from above in the vertical direction) may be recognized as the edge representing the upper eyelid. The position of the upper eyelid can be accurately detected by using such a characteristic shape. Alternatively, when a plurality of sequential image frames is used, the position of the upper eyelid may be detected by using the characteristic that the upper eyelid moves greatly during blinking in comparison with the other parts of the eye (such as the lower eyelid, eyebrow, or eyeglass frames).

In step S140, the position of the search window for detecting the lower eyelid is determined according to the position of the upper eyelid determined in step S130 above. The position of the search window for detecting the lower eyelid may be arranged below the upper eyelid with reference to the position of the upper eyelid detected as described above and, for example, arranged below the position of the upper eyelid for the number of pixels corresponding to the average size of eyes (average distance between the upper eyelid and the lower eyelid in a state where the eyes open). The size of the search window for detecting the lower eyelid may be the same size as the search window for detecting the upper eyelid and may be defined according to the pixel range that represents the lower eyelid and is derived from the experiment and the like in advance.

In step S150, the search window is moved to the position determined in step S140, and the position of the lower eyelid is determined. If there is a lateral edge (black-white edge) in the search window, such lateral edge is recognized as the lateral edge that represents the lower eyelid, for example.

In step S160, the vertical distance between the lateral edge recognized in step S130, which represents the upper eyelid, and the lateral edge recognized in step S150, which represents the lower eyelid, is calculated as the eye opening, and it is determined according to the eye opening whether the the driver's eyes are closed. The determination result may be used for various alarm controls. For example, the alarm may be output by detecting the length of time that the driver's eyes are closed and determining that the driver's level of consciousness falls when such length of time reaches the predetermined time or longer.

According to the eye opening detection system 100 of this embodiment as described above, the following effects can be proved in particular.

As described above, because the present invention detects the upper eyelid, determines the searching range of the lower eyelid with reference to the detection result of the upper eyelid, and detects the lower eyelid within the searching range, the detection accuracy of the lower eyelid is significantly improved in comparison with the construction for detecting the upper and the lower eyelids separately and independently or the construction for detecting the lower eyelid before detecting the upper eyelid. Specifically, the upper eyelid can be detected according to its characteristic in shape that the upper eyelid is in an arc shape at opening as described above, and therefore, it is easier to detect the upper eyelid than the lower eyelid, which has a poor characteristic in shape. In other words, the lower eyelid is harder to detect compared to the upper eyelid due to its poor characteristics. Therefore, detecting the upper eyelid first and then detecting the lower eyelid according to the detection result enable the lower eyelid, which has poor characteristics and is hard to be detected, to be detected more easily and accurately.

According to the above description, when the imaging means 120 captures the face of driver from below to acquire the face image, the eyelashes of the upper eyelid do not cover the eyeball. Thus, the lateral edge representing the upper eyelid can be easily extracted (that is, the lateral edge representing the upper eyelid can be clearly detected.) Consequently, the detection accuracies of the upper eyelid as well as the lower eyelid are significantly improved. When the imaging means 120 captures the face of driver upward from below to acquire the face image, there is a case that eyelashes of the lower eyelid may cover the eyeball and thus the lateral edge representing the lower eyelid cannot be clearly detected. In this point, however, because the embodiment of the present invention as described above detects the upper eyelid first and then detects the lower eyelid according to the detection result, the lateral edge representing the lower eyelid can be detected accurately even if it is unclear.

According to the above description that the lighting means 130 illuminates the face of driver from below to acquire the face image, a shadow is cast on the upper side. Thus, the lateral edge representing the upper eyelid is more easily extracted (that is, the lateral edge representing the upper eyelid can be clearly detected.). Consequently, the detection accuracies of the upper eyelid as well as the lower eyelid are significantly improved. When the lighting means 130 illuminates the face of driver from below to acquire the face image, there is a case that the shadow of the lower eyelid covers the eyeball and thus makes it more difficult to detect the lateral edge representing the lower eyelid. In this point, however, because the embodiment of the present invention as described above detects the upper eyelid first and then detects the lower eyelid according to the detection result, the lateral edge representing the lower eyelid can be detected accurately even if it is unclear.

In the embodiment described above, it may be considered that the "edge extraction means" of the present invention is realized with the image processing device 140 performing the processes in the step S120 of FIG. 2 and the "upper and lower eyelid detection means" of the present invention is realized with the image processing device 140 performing the processes in the step S130 and S140 of FIG. 2.

Although a detailed description of example embodiments of the present invention has been provided, the present invention is not limited to the described embodiments, and various modification and replacement to the described embodiments may be allowed without departing from the scope of the invention.

For example, the detected subject of the embodiment is a driver of a vehicle; however, an operator of a motorcycle, a railcar, or an aircraft may also be the detected subject.

In addition, although the eyelids are detected using the sum of the intensity of the lateral edge or the peak in the histogram (peak of the lateral edge) as the evaluation value in the above described embodiment, the upper and the lower eyelids may be detected by using pattern matching. In this case, performing the pattern matching in accordance with the characteristic in the arc shape of the upper eyelid improves the detection accuracy not only for the upper eyelid but also for the lower eyelid detected with reference to the upper eyelid.

Furthermore, the above described embodiment exemplifies the application using a single imaging means 120; however, a second imaging means may be provided separately from the imaging means 120, and two or more imaging means may be used to detect the eye opening of the driver. In this case, the second imaging means may be disposed in a sun visor or the rearview mirror, for example. The image processing device 140 may employ the method for detecting the lower eyelid with reference to the upper eyelid as described above for at least the image captured by the imaging means disposed in the lower side in the vertical direction. Furthermore, the construction selectively using a plurality of the imaging means may determine the selection of the imaging means and appropriately change the edge extraction method (as well as the upper and lower eyelid detection method) in response to the selection of the imaging means.

The invention claimed is:

1. An eye opening detection system comprising:
    first imaging means for acquiring an image of a face of a detected subject;
    edge extraction means for extracting an edge of the acquired image; and
    upper and lower eyelid detection means for detecting an upper eyelid and a lower eyelid of the detected subject according to the edge extracted,
    wherein an eye opening of the detected subject is determined with reference to a distance between the upper eyelid and the lower eyelid detected, and the upper and lower eyelid detection means detects the upper eyelid using a plurality of time sequential image frames based on greater upper eyelid movement during blinking than other parts of the eye, determines, with reference to a position of the detected upper eyelid, a position of a searching window for detecting the lower eyelid and then detects the lower eyelid by searching within the searching window located at the determined position.

2. The eye opening detection system according to claim 1, wherein
    the first imaging means is disposed in a position lower than eyes of the detected subject in a vertical direction.

3. The eye opening detection system according to claim 1, wherein
    the detected subject is an operator of a vehicle, and the first imaging means is disposed in a position lower than a headrest disposed on an operator's seat in a vertical direction.

4. The eye opening detection system according to claim 1, further comprising:
    lighting means for emitting light to the face of the detected subject, wherein
    the lighting means is disposed in a position lower than the eyes of the detected subject in a vertical direction.

5. The eye opening detection system according to claim 4, wherein
    the detected subject is an operator of a vehicle, and the lighting means is disposed in a position lower than a headrest disposed on an operator's seat in a vertical direction.

6. The eye opening detection system according to claim 1, further comprising:
    second imaging means provided separately from the first imaging means, wherein
    the edge extraction means extracts the edge of the image acquired by at least one of the first imaging means and the second imaging means, and
    the upper and lower eyelid detection means detects the upper eyelid with respect to the image acquired by at least the first imaging means between the first and the second imaging means and detects the lower eyelid as well with reference to the detected upper eyelid.

7. An eye opening detection method of detecting an eye opening of a detected subject, comprising:
    acquiring an image of a face of a detected subject;
    extracting an edge of the acquired image of the face;
    detecting an upper eyelid of the detected subject according to the edge extracted, the detection using a plurality of time sequential image frames and being based on greater upper eyelid movement during blinking than other parts of the eye;
    determining, with reference to a position of the detected upper eyelid, a position of a searching window for detecting the lower eyelid;
    detecting a lower eyelid of the detected subject by searching within the searching window located at the determined poison; and
    detecting an eye opening of the detected subject with reference to a distance between the detected upper and the lower eyelids.

8. An eye opening detection system comprising:
    a first imaging device that captures an image of a face of a detected subject;
    an edge extraction device that extracts an edge of the captured image; and
    upper and lower eyelid detection device that detects an upper eyelid of the detected subject according to the extracted edge using a plurality of time sequential image frames and based on greater upper eyelid movement during blinking than other parts of the eve, determines, with respect to a position of the detected upper eyelid, a position of a searching window for detecting a lower eyelid and detects the lower eyelid by searching within the searching window located at the determined position, wherein
    the eye opening detection system detects an eye opening of the detected subject with reference to a distance between the upper eyelid and the lower eyelid detected.

9. The eye opening detection system according to claim 8, further comprising:
    a nose detection device that detects a position of a nose of the subject within the image; and
    an eye detection device that detects a position of an eye of the subject based on the position of the nose.

10. The eye opening detection system according to claim 9, wherein the nose detection device detects the position of the nose based on identification of nostrils of the nose.

11. The eye opening detection system according to claim 10, wherein the eye detection device positions an upper eye window with respect to the nose position and the upper and lower eyelid detection device searches the upper eye window to detect the upper eyelid.

12. The eye opening detection system according to claim 11, wherein the upper and lower eyelid detection device identifies the upper eyelid as an edge within the upper eye window having an arc shape.

13. The eye opening detection system according to claim 11, wherein the upper and lower eyelid detection device discards an uppermost and a lowermost edge within the upper eye window before detection of the upper eyelid.

14. The eye opening detection system according to claim 11, wherein the upper and lower eyelid detection device searches the upper eye window using a search window of a size smaller than a size of the upper eye window, the upper and lower eyelid detection device calculating a position where a sum of lateral edge intensities is greatest as an upper eyelid candidate, the upper and lower eyelid detection device moving the search window within the upper eye window.

15. The eye opening detection system according to claim 14, wherein the upper and lower eyelid detection device discards uppermost and lowermost upper eyelid candidates within the upper eye window after searching the upper eye window with the search window.

* * * * *